(12) United States Patent
Dutova et al.

(10) Patent No.: US 8,337,416 B2
(45) Date of Patent: Dec. 25, 2012

(54) BIOPSY DEVICE

(75) Inventors: Tatjana Dutova, Limerick (IL); Shay Lavelle, Limerick (IL); Kenneth C. Kennedy, II, Limerick (IL); Arthur Thomas Henry, Dublin (IL)

(73) Assignee: Cook Medical Technologies LLC, Bloomington, IN (US)

( * ) Notice: Subject to any disclaimer, the term of this patent is extended or adjusted under 35 U.S.C. 154(b) by 179 days.

(21) Appl. No.: 12/842,444

(22) Filed: Jul. 23, 2010

(65) Prior Publication Data
US 2012/0022398 A1 Jan. 26, 2012

(51) Int. Cl.
*A61B 10/00* (2006.01)
(52) U.S. Cl. ........................................ 600/567
(58) Field of Classification Search ........... 600/562–568
See application file for complete search history.

(56) References Cited

U.S. PATENT DOCUMENTS

| | | | | |
|---|---|---|---|---|
| 3,692,020 | A * | 9/1972 | Schied | 600/568 |
| 4,095,667 | A | 6/1978 | Mahig et al. | 181/120 |
| 4,476,864 | A | 10/1984 | Tezel | 128/305 |
| 4,727,875 | A | 3/1988 | Dory | 128/328 |
| 4,958,625 | A | 9/1990 | Bates et al. | 128/754 |
| 5,160,336 | A | 11/1992 | Favre | 606/128 |
| 5,284,156 | A | 2/1994 | Schramm et al. | 128/754 |
| 5,415,182 | A | 5/1995 | Chin et al. | 128/754 |
| 5,476,101 | A | 12/1995 | Schramm et al. | 128/754 |
| 5,507,298 | A | 4/1996 | Schramm et al. | 128/754 |
| 5,722,980 | A | 3/1998 | Schulz et al. | 606/128 |
| 5,868,756 | A | 2/1999 | Henry et al. | 606/128 |
| 6,283,925 | B1 * | 9/2001 | Terwilliger | 600/568 |
| 6,436,054 | B1 * | 8/2002 | Viola et al. | 600/562 |

(Continued)

FOREIGN PATENT DOCUMENTS
EP 0 318 447 A1 11/1988
(Continued)

OTHER PUBLICATIONS
Lindgren, P.G., Percutaneous Needle Biopsy, ACTA Radiologica Diagnosis, Fasc 6, 4 pages.

(Continued)

*Primary Examiner* — Jeffrey G Hoekstra
*Assistant Examiner* — Megan Leedy
(74) *Attorney, Agent, or Firm* — Brinks Hofer Gilson & Lione

(57) ABSTRACT

A mechanism for sequentially loading and unloading a biopsy instrument includes a first wheel operatively connected with a cannula, the first wheel being rotatably mounted upon an axle such that the axle urges rotation of the first wheel in a first direction to transfer the cannula and the first wheel to a loaded position, the first wheel being configured for selective rotation with respect to the axle in a second direction to transfer the cannula and the first wheel to an unloaded position. A second wheel is operatively connected with a stylet, the second wheel being configured to be rotated by the axle in the first direction when the first wheel is in the loaded position, the second wheel configured for rotation relative to the axle to transfer the stylet and second wheel from the loaded to unloaded position. The second wheel is operatively engaged with the first wheel to allow partial rotation of the second wheel in the second direction with respect to the first wheel and urging similar rotation of the first wheel in the second direction after at least some duration of relative rotation of the second wheel with respect to the second wheel.

21 Claims, 12 Drawing Sheets

U.S. PATENT DOCUMENTS

| | | | |
|---|---|---|---|
| 6,511,485 B2 | 1/2003 | Hirt et al. | 606/128 |
| 7,351,210 B2 | 4/2008 | Cicenas et al. | 600/564 |
| 7,470,274 B2 | 12/2008 | Lebet | 606/128 |
| 7,517,322 B2 * | 4/2009 | Weikel et al. | 600/566 |
| 7,854,707 B2 * | 12/2010 | Hibner et al. | 600/567 |
| 7,896,817 B2 * | 3/2011 | Garrison | 600/566 |
| 2005/0054947 A1 * | 3/2005 | Goldenberg | 600/567 |
| 2006/0089565 A1 * | 4/2006 | Schramm | 600/568 |
| 2006/0247669 A1 | 11/2006 | Lebet | 606/167 |
| 2007/0032742 A1 * | 2/2007 | Monson et al. | 600/566 |
| 2007/0239067 A1 * | 10/2007 | Hibner et al. | 600/567 |
| 2009/0171243 A1 * | 7/2009 | Hibner et al. | 600/566 |
| 2010/0210966 A1 * | 8/2010 | Videbæk | 600/564 |
| 2011/0201964 A1 * | 8/2011 | Speeg et al. | 600/562 |

FOREIGN PATENT DOCUMENTS

| | | |
|---|---|---|
| WO | WO 83/03343 | 10/1983 |
| WO | WO 88/07839 | 10/1988 |
| WO | WO 95/30377 | 11/1995 |
| WO | WO 01/52742 A1 | 7/2001 |
| WO | WO 2010/086741 A1 | 8/2010 |

OTHER PUBLICATIONS

Cook Urological, Inc., Cook® Bx Core Tissue Biopsy Device and Needle, 2010, 5 pages.

Bard Radiology, Introducing the Expa Biopsy System, 2 pages.

U.S.P.T.O., Office Action dated Jun. 12, 1998, U.S. Appl. No. 08/846,690, 13 pages.

* cited by examiner

BIOPSY DEVICE

TECHNICAL FIELD

This application relates to devices suitable for obtaining a tissue biopsy sample from tissue disposed within a patient, such as tissue within an internal organ or volume that is either accessible through a natural orifice of the patient, percutaneously, or laparoscopically. Biopsy devices that include an elongate stylet that is movably disposed within a cannula, with the stylet and then cannula sequentially and rapidly projected into a patient's tissue are often used to obtain biopsy samples.

BRIEF SUMMARY

A first representative embodiment of the disclosure is provided. The representative embodiment is a biopsy instrument for obtaining a tissue biopsy sample. The instrument includes a housing that movably supports one or more elongate stylets and one or more elongate cannulas, each cannula comprises a lumen through which one of the plurality of stylets is movably disposed therethrough. An operator is rotatably mounted to the housing about an axis and fixed to an axle. A first wheel is rotatable about the axis and in selective rotational connection with the axle, the first wheel is operatively engaged with the plurality of cannulas to cause translation of the cannulas with rotation of the first wheel. A second wheel is rotatable about the axis and in selective rotational connection with the axle, the second wheel is operatively engaged with the plurality of stylets to cause translation of the stylets with rotation of the second wheel. A shuttle is disposed upon the housing and in selective connection with the first and second wheels, the shuttle being translatable about the housing in a direction substantially parallel to the axis, the shuttle comprising a pin that is received within a first slot defined about an outer circumference of the first wheel and selectively engageable with the second wheel to selectively allow torque transfer from the axle to the second wheel.

A second representative embodiment of the disclosure is provided. The representative embodiment is a biopsy instrument. The biopsy instrument includes a housing that encloses a translatable cannula carrier and a translatable stylet carrier, the stylet carrier is disposed within at least a portion of the cannula carrier. One or more stylets are fixed to the stylet carrier with a portion extending from the housing and one or more cannulas are fixed to the cannula carrier, and the one or more cannulas each extend from the housing with each of the one or more cannulas receiving a portion of one of the plurality of stylets within a lumen of the cannula. The instrument additionally includes a stylet and cannula operation mechanism with a first wheel rotatably disposed within the housing upon an axle and a second wheel rotatably disposed within the housing upon the axle and rotatable with respect to the first wheel. A first connecting rod is pivotably connected to each of the first wheel and the cannula carrier on opposite ends thereof and a second connecting rod is pivotably connected to the second wheel and the stylet carrier on opposite ends thereof. An operator is rotatably disposed upon the housing and configured such that a first rotation of the operator from a rest position causes the first wheel to rotate in a first direction until a line through the opposite ends of the first connecting rod extends through the axle, and such that a second rotation of the operator in the first direction causes the second wheel to rotate in the first direction until a second line through the opposite ends of the second connecting rod extends through the axle.

A third representative embodiment of the disclosure is provided. The representative embodiment is a mechanism for sequentially loading and unloading a biopsy instrument. The mechanism includes a first wheel operatively connected with a cannula, and that is rotatably mounted upon an axle such that the axle urges rotation of the first wheel in a first direction to transfer the cannula and the first wheel to a loaded position, the first wheel being configured for selective rotation with respect to the axle in a second direction to transfer the cannula and the first wheel to an unloaded position. A second wheel is operatively connected with a stylet, the second wheel being configured to be rotated by the axle in the first direction when the first wheel is in the loaded position, the second wheel also configured for rotation relative to the axle to transfer the stylet and second wheel from the loaded to unloaded position. The second wheel is operatively engaged with the first wheel to allow partial rotation of the second wheel in the second direction with respect to the first wheel and urging similar rotation of the first wheel in the second direction after at least some duration of relative rotation of the second wheel with respect to the second wheel.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 10b is a front view of the components of FIG. 10a.

FIG. 11b is a front view of the components of FIG. 11a.

DETAILED DESCRIPTION OF THE DRAWINGS AND THE PRESENTLY PREFERRED EMBODIMENTS

Figure 1:
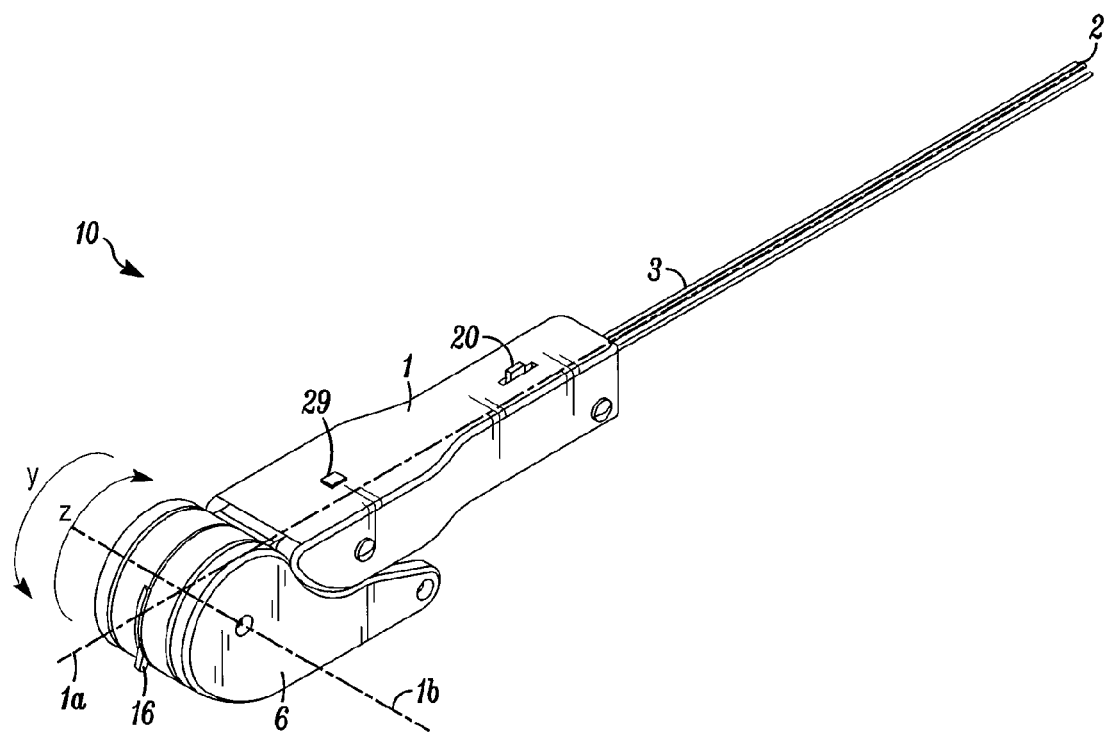
FIG. 1 is a perspective view of biopsy instrument in a rest configuration.

Turning now to FIGS. 1-11c, a biopsy instrument 10 is provided. The instrument 10 may be configured to obtain a single biopsy sample using a stylet or needle 2 that is movably positioned within a lumen of a cannula 3. In some embodiments, the instrument 10 may include a single assembly of stylet and cannula 2, 3, while in other embodiments, the device 10 may be configured with multiple stylets and cannulas 2, 3 that are configured to simultaneously obtain multiple biopsy tissue samples in close proximity to each other.

Figure 1A:
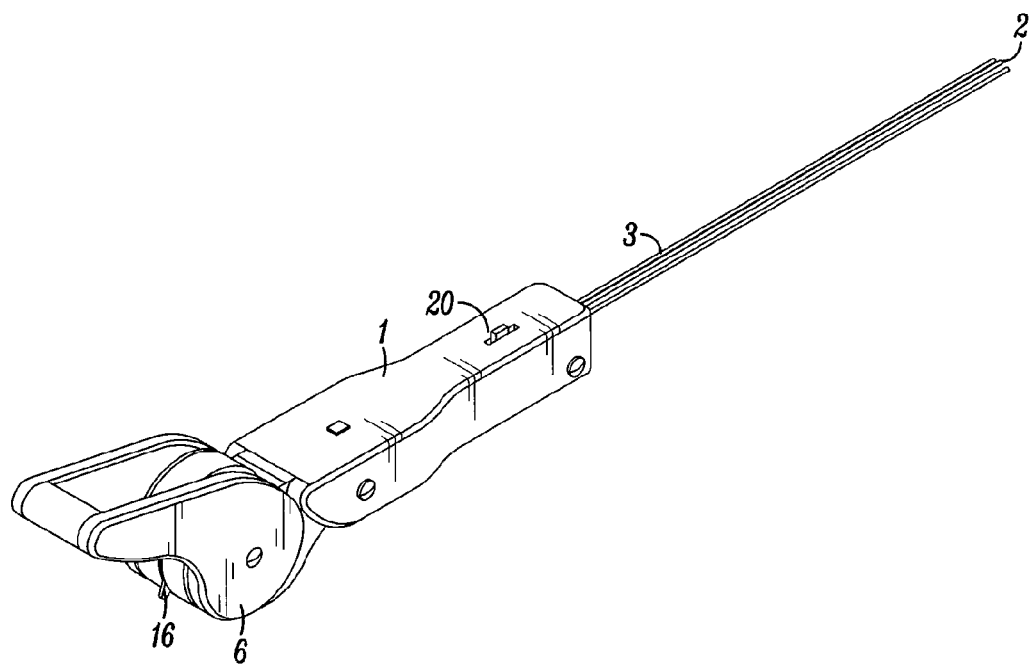
FIG. 1a is the view of FIG. 1 with the cannulas of the instrument in the loaded position and the stylets in the rest position.

The stylet 2 is an elongate member that may include a beveled or sharpened distal end. The stylet 2 may additionally include a trough disposed proximate the distal end thereof. The stylet 2 is independently translatable within a lumen within the cannula 3 and the cannula 3 is additionally independently translatable with respect to the stylet 2. The stylet and cannula 2, 3 are disposed in concert with the instrument 10 for three potential configurations, both partially retracted within the housing 1 of the instrument 10, the stylet 2 extended form the housing 1 with the cannula 3 loaded within the housing (FIG. 1a), and the cannula 3 and stylet 2 each extended from the housing 1 (FIG. 1). In some embodiments, the stylet 2 and cannula 3 may be each independently biased toward the extended position with springs disposed within the housing 1.

In operation, the instrument 10 is positioned with respect to the patient normally with the stylet 2 and cannula 3 each in the retracted position. Specifically, the distal tips of the stylet 2 and cannula 3 are positioned proximate to the location where the patient's tissue sample is desired. With the instrument 10 properly positioned, the instrument 10 is fired by the user, which initially releases the stylet 2 from its withdrawn position, such that the distal end of the stylet 2 rapidly moves forward with respect to the cannula 3 due to the biasing force imparted thereon, until the distal tip and trough become exposed from the distal end of the cannula 3. The sharpened or beveled tip of the stylet 2 causes the stylet 2 to penetrate the patient's tissue, with a portion of the patient's tissue proximate the trough being moved to within the void created by the trough. After sufficient forward motion of the stylet 2, the cannula 3 is released from its withdrawn position and rapidly moves forward with respect to the cannula 3 until the cannula 3 again covers the trough and at least a portion of the distal tip of the stylet 2. In some embodiments, the instrument 10 is configured to automatically release the cannula 3 for forward travel when the stylet 2 either approaches or reaches its fully forward position.

The rapid motion of the cannula 3 over the trough causes the tissue disposed within the void in the stylet 2 formed by the trough to be sheared from the neighboring tissue and remain within the trough to collect the tissue sample. Upon completion of the firing sequence, the instrument 10 may be manipulated to retrieve the tissue sample therefrom by manipulating the instrument to withdraw the cannula 3 and again uncover the distal end and the trough of the stylet 2, whereby the instrument 10 may be repositioned for another tissue sample. In embodiments with multiple sets of stylets 2 and cannulas 3, the distal tips of the stylets and cannulas from each set are positioned proximate to each other and are moved simultaneously (as described above) to simultaneously obtain multiple closely spaced tissue sample from the patient.

The instrument 10 further includes a housing 1 that encloses and supports the moving components of the stylet 2 and cannula 3 mechanisms and provides the preferably ergonomically shaped and sized component that is held by the user. The instrument further includes a rotational loading mechanism with a first, or cannula wheel 40 that is operatively engaged with the one or more cannulas 3 through a first connecting rod 30 and a cannula carrier 14, and a second or stylet wheel 50 that is operatively engaged with the one or more stylets 2 with a second connecting rod 36 and a stylet carrier 15. The first and second wheels 40, 50 are each independently rotatably mounted upon an axis 1b that extends through the housing 1 in a direction substantially perpendicular to the line of action 1a of the one or more stylet and cannulas 2, 3. The instrument further includes a shuttle 60 that is movably disposed within the housing 1 in a direction substantially parallel to the axis 1b, with the shuttle 60 being operatively engaged with each of the first and second wheels 40, 50. The position of the shuttle 60 with respect to the second wheel 50 determines the potential rotation of the second wheel 50 and engagement between the shuttle 60 and first wheel 40 determines the range of motion of the first wheel 40. The instrument additionally includes an operator 6 that is fixed to an axle 18 that extends through central apertures 41, 51 (FIG. 2) in each of the first and second wheels 40, 50, and with the relative position of the first and second wheels 40, 50 and shuttle 60 determining the rotational connection between the operator 6 and the first and second wheels 40, 50.

The instrument 10 further includes a safety 16 that is movably mounted to the housing 1 and selectively engageable with the first and second wheels 40, 50 to prevent spurious and unintended forward translational motion of the stylet 2 and cannula 3. The instrument 10 additionally includes a firing mechanism 20 that is disposed upon the housing 1 to allow for automated and rapid forward motion of the one or more stylets and cannulas 2, 3 with respect to the housing 1 to obtain a desired tissue sample.

Figure 2:
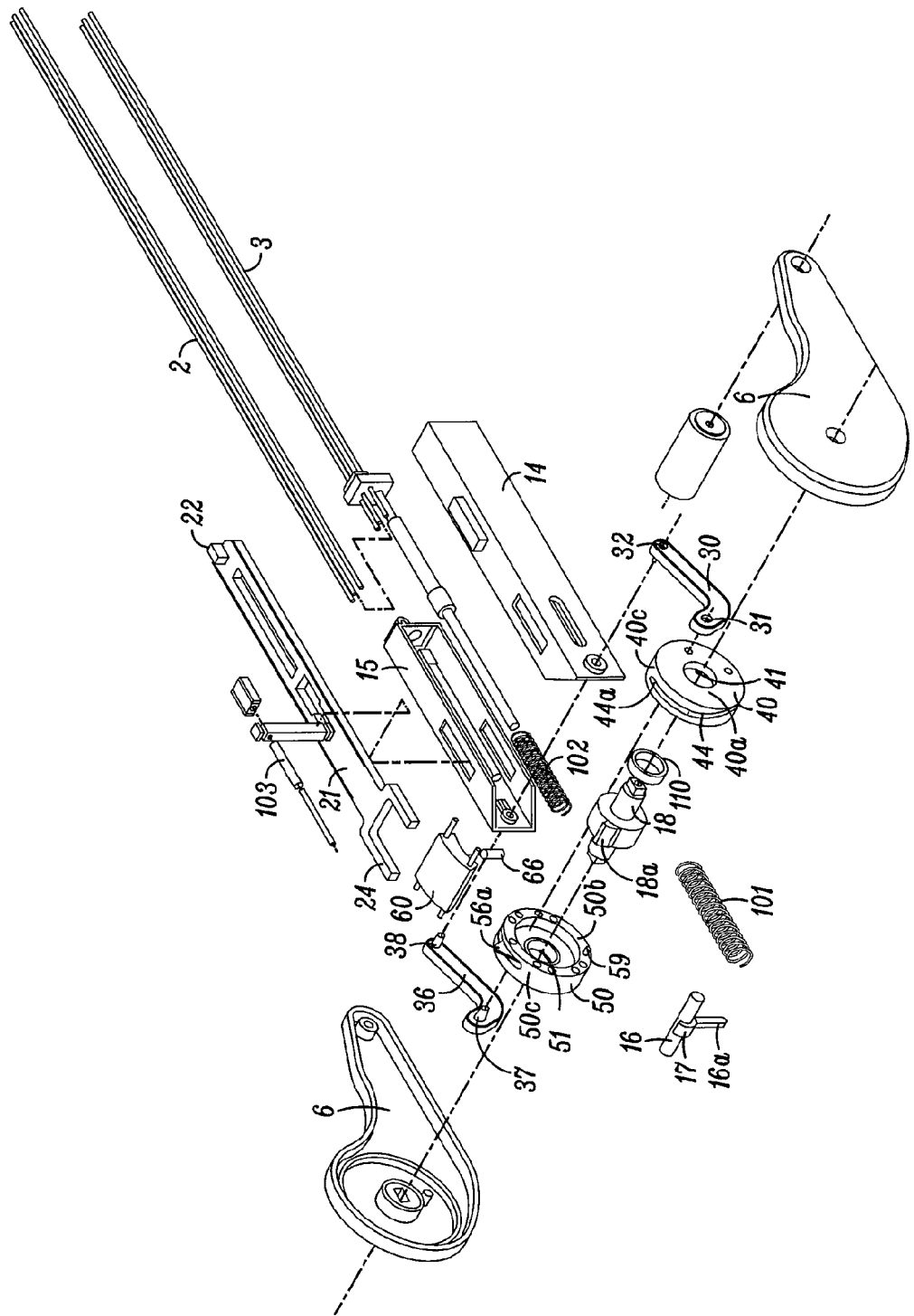
FIG. 2 is an exploded view of the instrument of FIG. 1.
Figure 3:
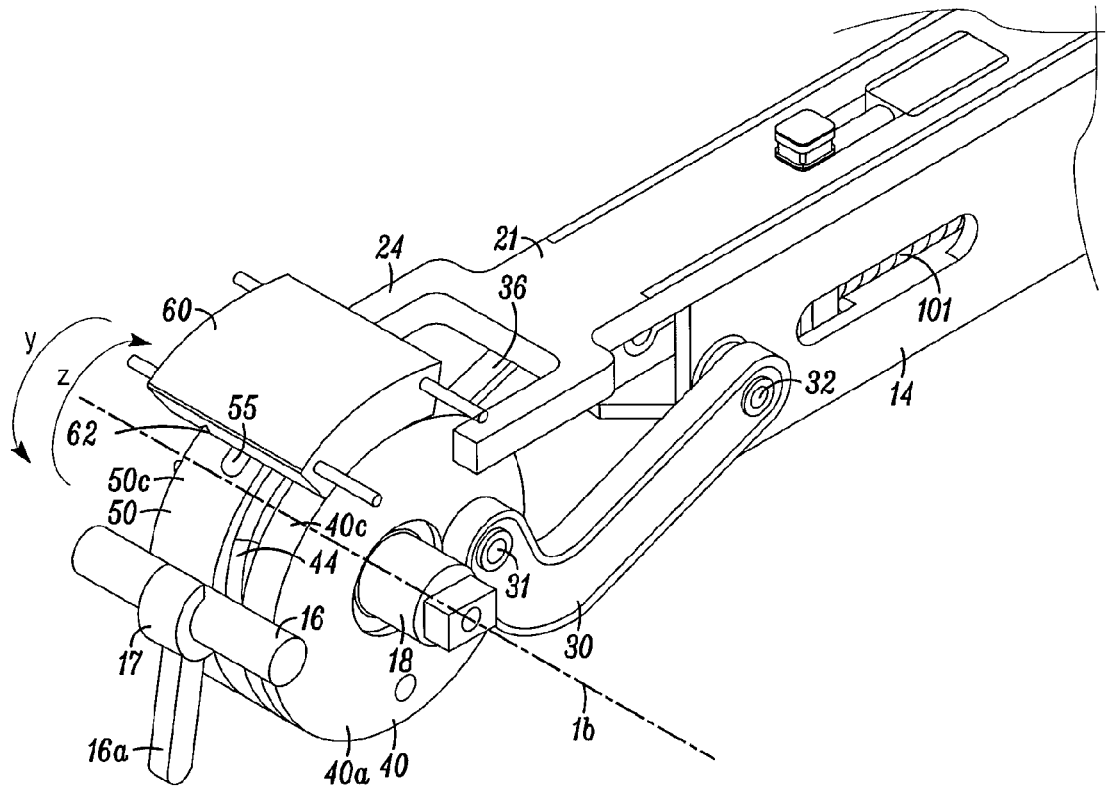
FIG. 3 is a perspective view of the instrument of FIG. 1 with the housing removed, showing the first wheel and related components with the instrument in the rest configuration.
Figure 3A:
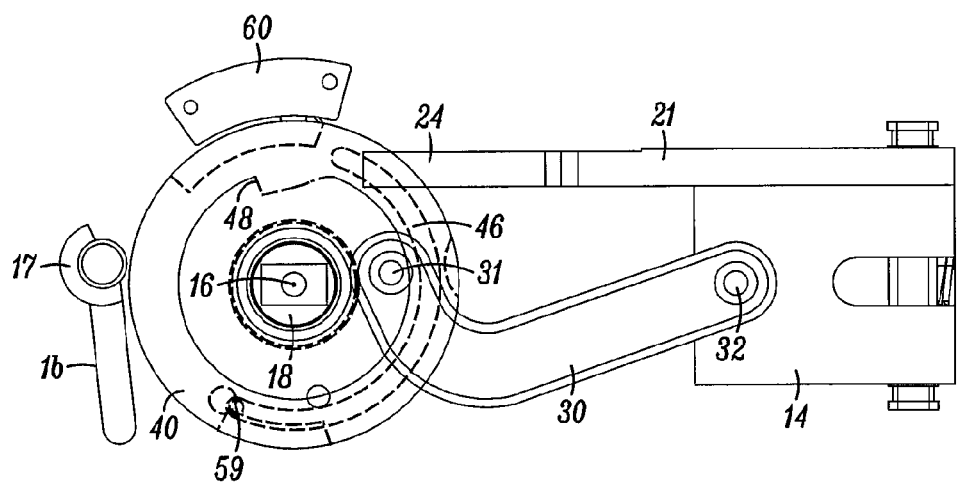
FIG. 3a is a side view of the configuration of FIG. 3.
Figure 6:
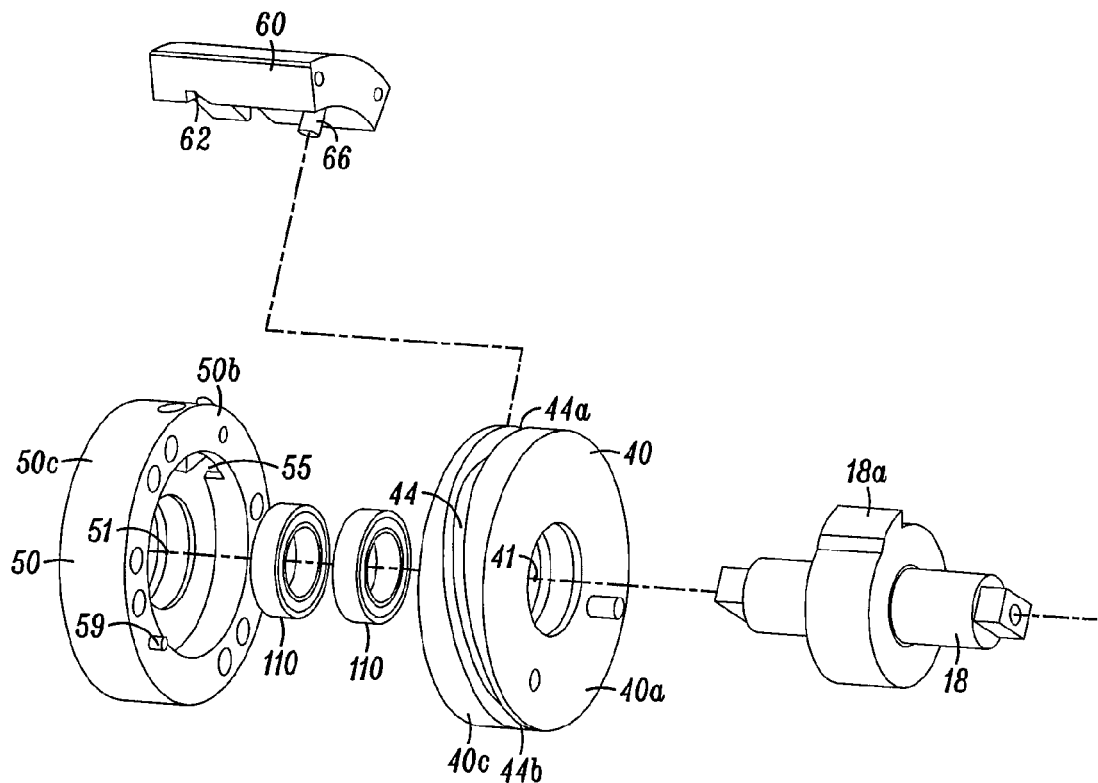
FIG. 6 is an exploded view of the first wheel, second wheel, shuttle, and axle.

With reference to FIGS. 2, 3, and 6, the first and second wheels 40 and 50 are each rotatably mounted to the housing 1 about the axle 18 with one or more bearings or bushings 110 such that in some relative positions of the wheels 40, 50 and the axle 18, the rotation of the axle 18 (due to similar rotation of the operator 6) causes rotation of one of the first or second wheels 40, 50, while in other positions rotation of the axle 18 causes rotation of the other of the first and second wheels 40, 50, while in still other relative configurations rotation of the axle 18 does not cause rotation of the first and second wheels 40, 50. As best shown in FIGS. 2 and 6, the axle 18 is a cylindrical member that includes a tooth 18a that extends radially from a portion of the circumference of the axle 18 at a specific location upon the axle 18 to provide selective operative engagement with each of the first and second wheels 40, 50.

Figure 7:
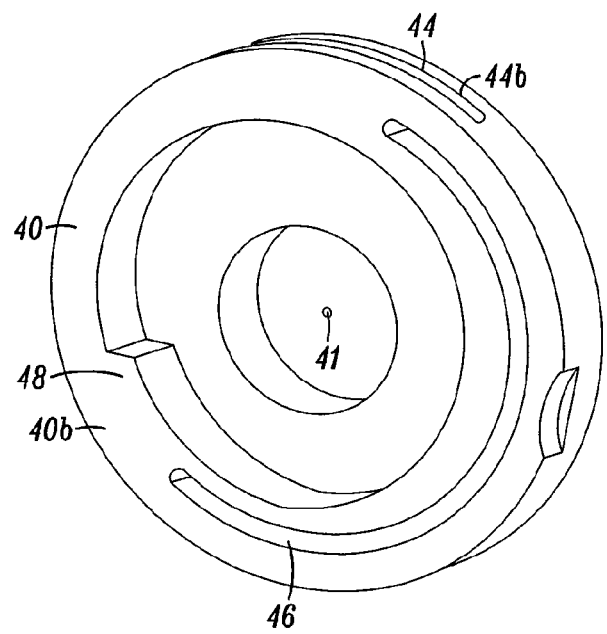
FIG. 7 is a perspective view of the first wheel.

The first wheel 40 is a circular member with a central hole 41 to receive the axle 18 therethrough. The first wheel 40 is mounted to the axle 18 with one or more bearings or bushings to allow partial relative rotation of the first wheel 40 with respect to the axle 18 and vice versa. As shown in FIG. 7, the inner surface 41 of the first wheel 40 includes a ledge 48 that extends radially inward through a portion of the open center 41 of the wheel 40, with the ledge 48 selectively engaged by the tooth 18a of the first wheel 40 in a specific configuration of the instrument 10. Specifically, in some embodiments, the tooth 18a of the axle 18 engages the ledge 48 when the cannula 3 is in the extended position (FIG. 1). When the tooth 18a and ledge 48 are engagement, rotation of the operator 6 about the housing 1 will cause similar rotation of the first wheel 40 in the direction Z.

The outer circumference of the first wheel 40 includes a first slot 44 that is blindly formed along a portion of the outer circumferential surface first wheel 40. The first slot 44 may have a constant depth along its length or in other embodiments the first slot 44 may have varying depths along its length. In some embodiments, the first slot 44 may be formed upon about half of the circumference of the wheel 40 (i.e. 180 degrees of arc length), while in other embodiments the first slot 44 may be formed about from about, and inclusive of, about 150 degrees to about 210 degrees). As will be appreciated with reference to the discussion of the shuttle 60 below, the arc length of the first slot 44 defines the range of potential rotation of the first wheel 40 with respect to the shuttle 60, and therefore with respect to the housing 1.

The first slot 44 is additionally curved along the outer circumferential surface 40c of the first wheel 40, such that a first end 44a of the first slot 44 (FIG. 6) is proximate the inner surface 40b of the first wheel 40 and the opposite second end 44b of the first slot 44 is proximate the outer surface 40a of the first wheel 40. As discussed further below, a rod 66 extending from a lower surface of the shuttle 60 may be disposed within the first slot 44. Because the first slot 44 is curved along its length, rotation of the first wheel 40 urges the shuttle 60 to translate in a direction parallel to the rotational axis 1b of the first wheel 40. Specifically, the first slot 44 is configured such that the shuttle 60 translates in a direction W away from the second wheel 50 and toward the first wheel 40 when the first wheel 40 rotates in the first direction Z and translates toward the second wheel 50 in a direction X when the first wheel rotates in the second direction Y. The first slot 44 may be formed with a constant curvature along its length, or in other embodiments shown in FIG. X, the central portion of the first slot 44 has a larger or more dramatic curve than the opposite end portions 44a, 44b of the first slot 44, causing the shuttle 60 to translate relatively rapidly during the middle of the rotation of the first wheel 40, with a more gradual translation near the beginning and ending of the rotation of the first wheel 40.

The first wheel 40 additionally may include a second slot 46 shown in FIG. 7. The second slot 46 is arcuately disposed with a constant radius upon an inner side surface 40b of the first wheel 40, i.e. the surface that faces the neighboring second wheel 50 and has an arc length along a portion of the inner side surface 40b. The arc length of the second slot 46 defines the potential relative rotation between the first and second wheels 40, 50 because a peg 59 that extends outward from an inner side surface 50b of the second wheel 50 is disposed within the second slot 46. In some embodiments, the arc length of the second slot 46 is about the same as the arc length of the first slot 44, which allows the first and second wheels to rotate independently if each other for about the same arc length. In other embodiments it may be desirable to allow one of the first and second wheels 40, 50 to rotate along a greater arc length (and therefore allow the respective one or more stylets 2 or cannulas 3 to translate a greater distance than the other of the one or more stylets 2 or cannulas 3). In embodiments where the one or more cannulas 3 are desired to translate a greater distance than the one or more stylets 2, the arc length of the first slot 44 is greater than the arc length of the second slot 46, while in opposite situations where it is desired to translate the one more stylets 2 further than the one or more cannulas 3 the second slot 46 has a greater arc length. In other embodiments, the second wheel 50 may include a slot similar to the second slot 46 upon the first wheel 40 and the first wheel 40 may include a peg that extends within the slot upon the second wheel to constrain the relative rotation of the first and second wheels 40, 50 in a similar manner to that discussed herein.

The second wheel 50 is a circular member with a central hole 51 to receive the axle 18 therethrough. The inner surface 50b of the second wheel 50 includes a peg 59 that extends therefrom and is received within the second slot 46 in the first wheel 40, such that relative rotation between the first and second wheels 40, 50 is possible when the peg 59 is not disposed at one of the opposite ends of the second slot 46. As discussed in further detail below, the relative position of the peg 59 and the second slot 46 on the first wheel 40 determines when during the rotation of the second wheel 50 in the Y direction (which as discussed below causes forward motion of the one or more stylets 2) the peg 59 will engage an end of the second slot 46 of the first wheel 40 and urge similar rotation of the first wheel 40 in the direction Y (causing forward motion of the one or more cannulas 3).

The second wheel 50 additionally includes a boss 59a (FIG. 8) that extends outwardly from the outer side surface 50a of the second wheel 50. The boss 59a is configured to be aligned in close registration with a proximal tip 24 of a movable fork 21 (discussed in detail below) when the second wheel 50 is in the loaded position (FIG. 9). As discussed below, rearward impact upon the boss 59a by the proximal tip 24 of the fork 21 causes the second wheel 50 to rotate in the direction Y from the loaded position, which causes the second wheel 50 to return to the rest position (FIG. 8) from the loaded position, and therefore causes the one or more stylets 2 to rapidly translate forwardly to the extended position. Specifically, impact upon the boss 59a rotates second wheel 50 away from the loaded position, where the opposite ends 37, 38 of the second connecting rod 36 are aligned through the axis 1b. As the second wheel 50 rotates in the direction Y, the line of action through the opposite ends 37, 38 of the second connecting rod 36 no longer extends through the axle 18 and therefore the forward biasing force imparted upon the second connecting rod 36 creates a torque in the direction Y upon the second wheel 50. In some embodiments, the second wheel 50 (and/or the first wheel 40) may include one or more weights 53 strategically located within apertures in the second wheel, the weights being configured to increase the rotational inertia of the second wheel 50 (and one or more stylets 2) and therefore the momentum and impact force applied at the distal tip and trough of the stylet 2 to increase the effectiveness of the stylet 2 boring into the patient's tissue (and/or increasing the velocity and impact force of the one or more cannulas 3 onto the patient's tissue as it slides over the distal end of the stylet 2). Another benefit of the weights 53 is that the rotational momentum of the second wheel 50 is increased to impact from the peg 59 of the second wheel 50 upon and end of the second slot 46 of the first wheel 40, as discussed below, to cause the first wheel 40 to rotate in the first direction out of the over center position, as discussed below.

Figure 11A:
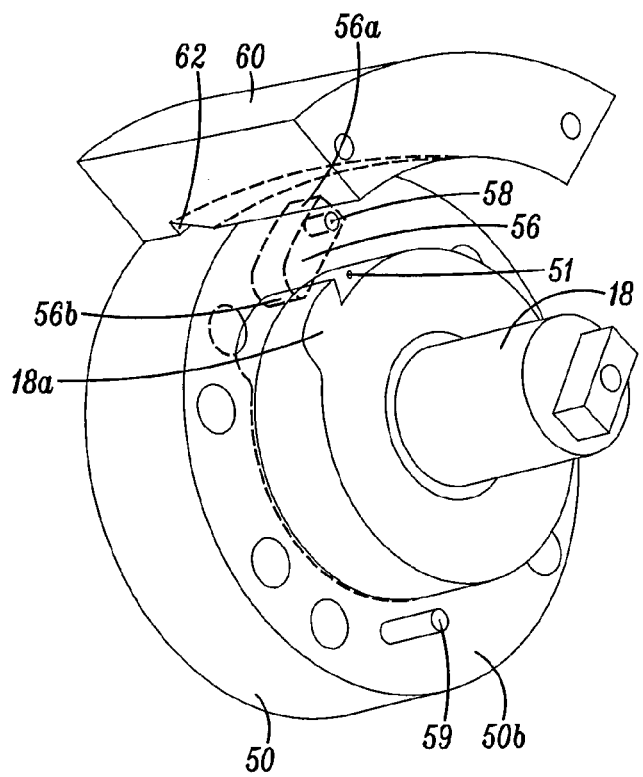
FIG. 11a is the view of FIG. 10a when the first wheel (not shown) is in the loaded configuration urging the shuttle to rotate the pawl toward engagement with the tooth of the axle.
Figure 11B:
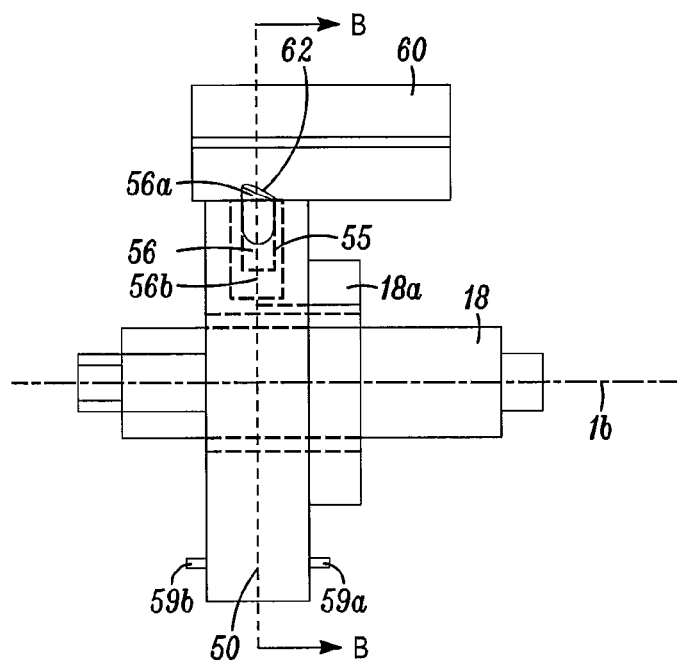
Figure 11C:
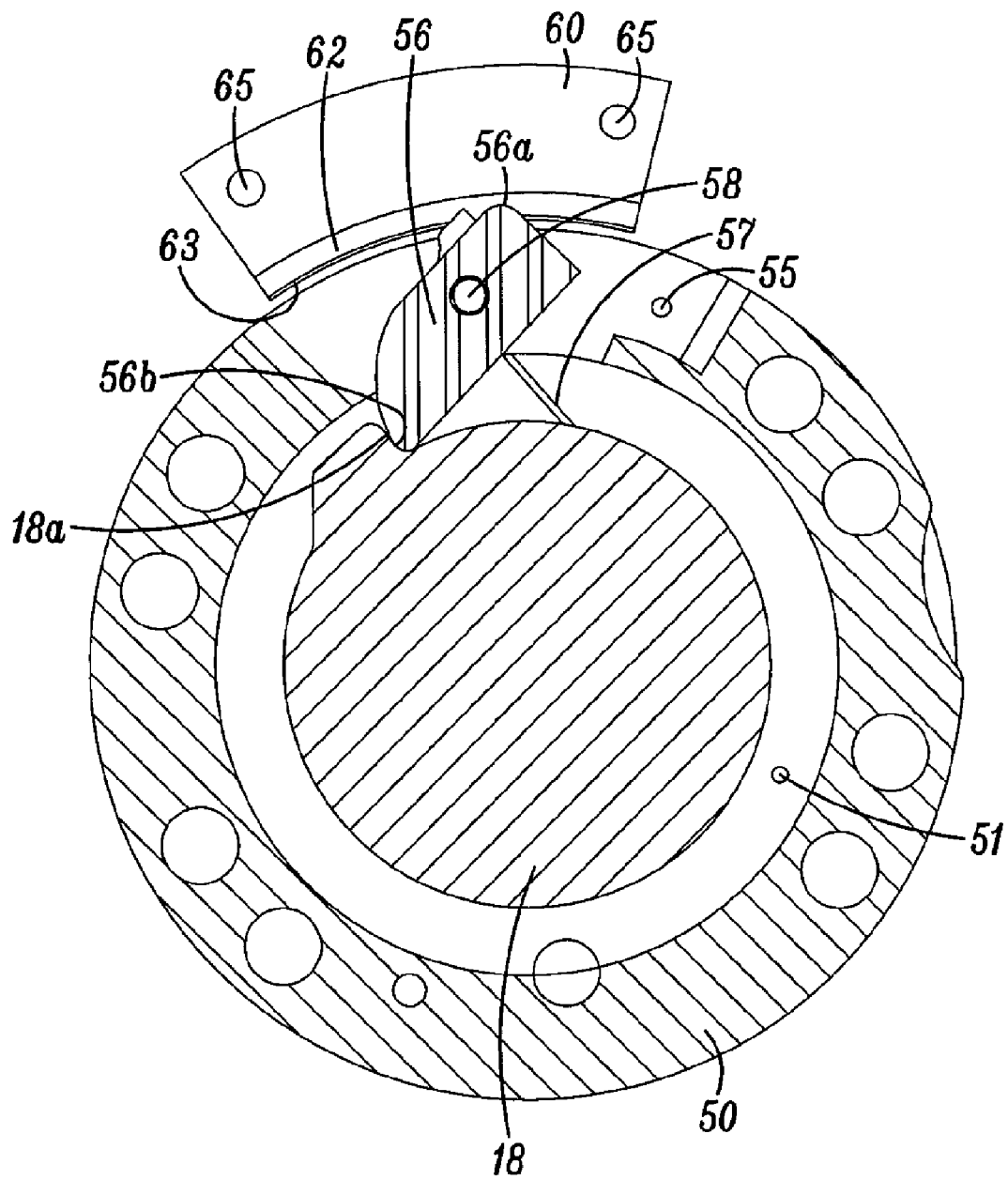
FIG. 11c is a sectional view of the components of FIG. 11b along the section B-B.

The second wheel 50 additionally supports a pawl 56 that is pivotably to the first wheel 50 with a pinned connection 58 and is disposed within a cutout 55 blindly defined within the second wheel 50. The pawl 56 includes an upper engagement portion 56a and a forward engagement portion 56b. The pawl 56 may be biased with a helical spring 57 or the like such that the forward engagement portion 56b is urged toward the open center 51 of the first wheel 50. When the instrument 10 is assembled, the axle 18 extends through the open center 51 of the second wheel 50 such that the pawl 56 is urged toward contact with the axle 18, and specifically toward engagement with the tooth 18a when the instrument is aligned as shown in FIGS. 11a-11c (i.e. in the orientation where the one or more cannulas 3 are fully loaded within the housing 1 but the one or more stylets 2 are extended). The biasing of the pawl 56 toward the axle 18 positions the pawl 56 in a rotational alignment with respect to the second wheel 50 such that the upper engagement portion 5a extends outside of the circumferential edge 51c of the second wheel 50.

Figure 10A:
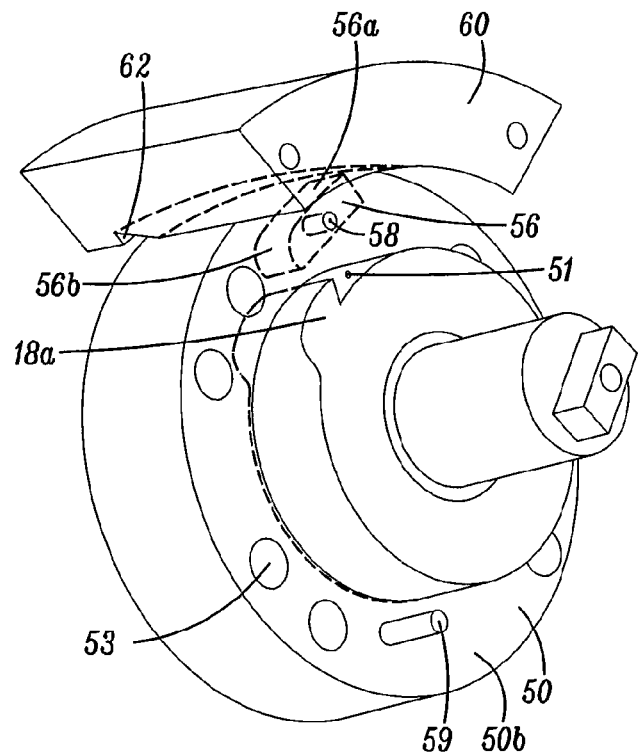
FIG. 10a is a perspective view of the second wheel, axle, and shuttle when the instrument is in the rest configuration.
Figure 10B:
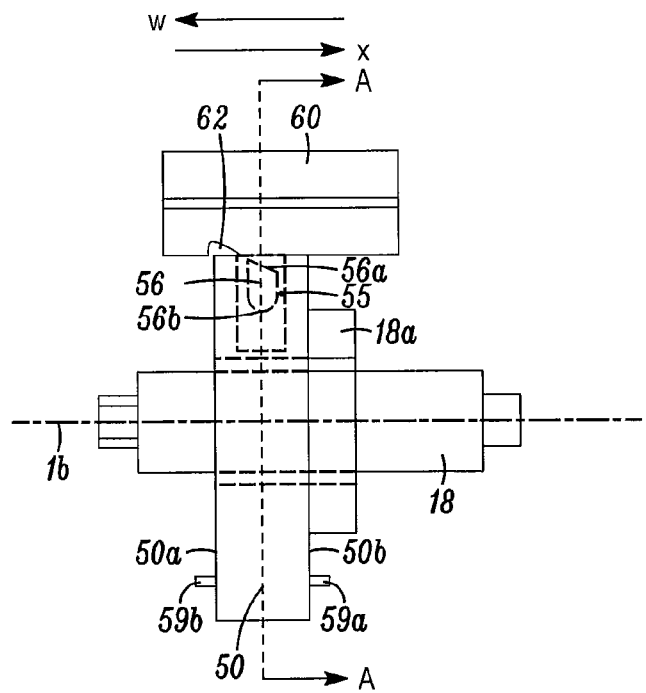
Figure 10C:
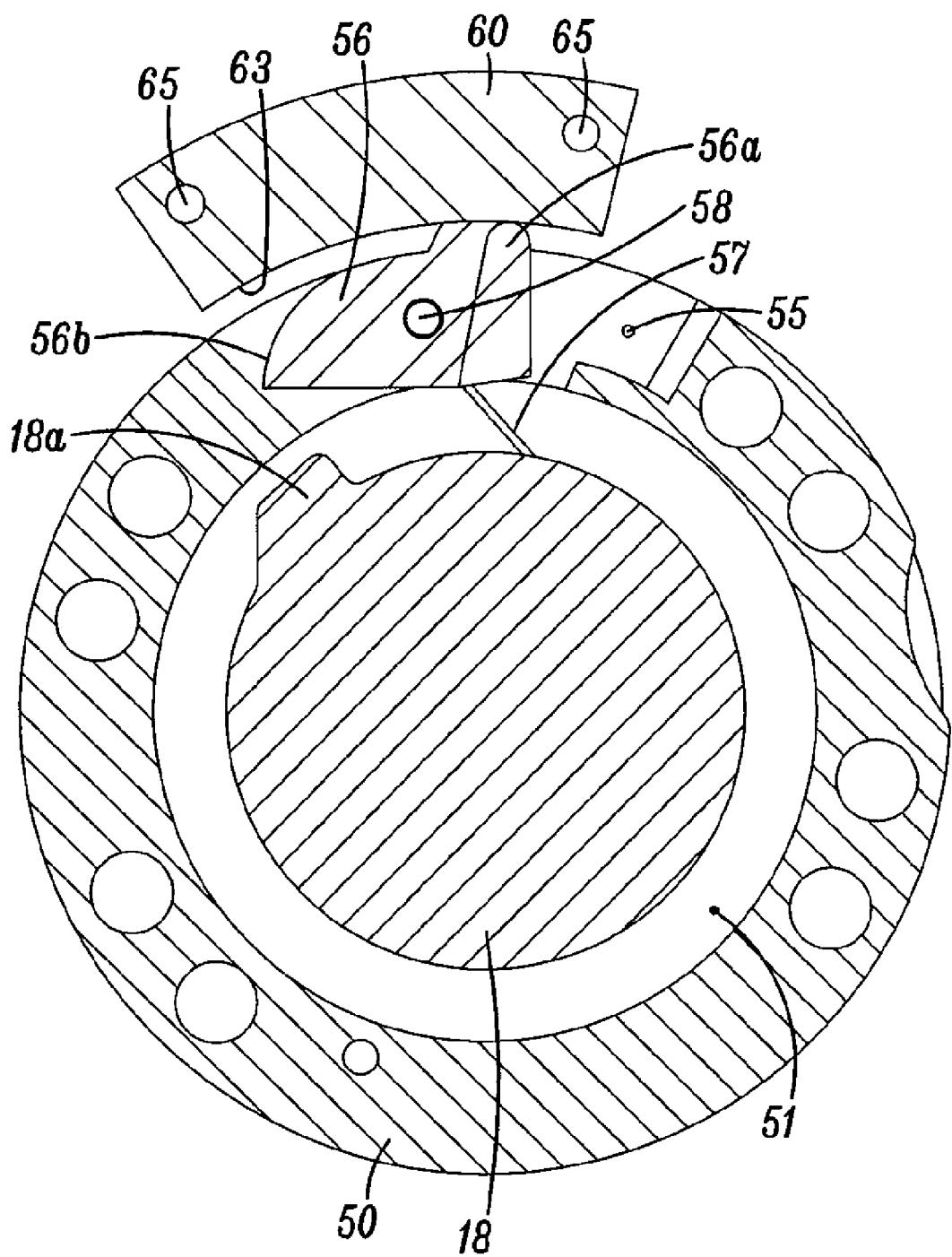
FIG. 10c is a sectional view of the components of FIG. 10b along the section A-A.

As best shown in FIGS. 6 and 10a-11b, the shuttle 60 is translatably mounted to the housing 1 such that the concave inner surface of the shuttle 60 is proximate to and of a similar curvature to the outer circumferential edge 51c of the second wheel 50 (as well as in some embodiments the outer circumferential edge 41c of the first wheel 40). As shown in FIGS. 10a-10c, when the instrument 10 is in the rest position (i.e. with the one or more stylets 2 and cannulas 3 each fully extended outward) the shuttle 60 is oriented such that the upper engagement portion 56a of the pawl 56 contacts the inner surface of the shuttle 60, preventing the upper engagement surface 56a from extending much past the outer circumferential edge 51c of the second wheel 50. Accordingly, the forward engagement surface 56b of the pawl 56 is maintained in the position shown in FIG. 10c, above the upper surface of the tooth 18a of the axle 18. In this orientation of the pawl 56 with respect to the second wheel 50, the pawl 56 is prevented from engaging the tooth 18a of the axle 18, which allows the axle 18 to rotate with respect to the second wheel 50.

As discussed above, rotation of the first wheel 40 urges the shuttle 60 to translate in a line substantially parallel to axis 1b due to the sliding contact between the rod 66 and the curved first slot 44 on the first wheel 40, which changes the position of engagement between the upper engagement portion 56a of the pawl 56 and the shuttle 60. The inner surface of the shuttle 60 includes a track 62 that is defined blindly within the shuttle 60. The track 62 is positioned upon the shuttle 60 such that the upper engagement portion 56a of the pawl 56 extends within the track 62 when the shuttle 60 has reached the end of its potential travel toward the first wheel 40 (FIGS. 5, 11a-11c), i.e. when the first wheel 40 is fully rotated to the loaded position with the rod 66 contacting the second end 44b of the first slot 44. The movement of the upper engagement portion 56a of the pawl 56 into the track 62 (as urged by the biasing member 57) allows the forward engagement portion 56b of the pawl 56 to rotate toward a position proximate the outer surface of the axle 18 and such that the forward engagement surface 56b of the pawl 56 can engage the tooth 18a. Engagement between the tooth 18a and the pawl 56 causes the axle 18 to urge rotation of the second wheel 50 in the direction Z when the operator 6 is similarly rotated in that direction. As discussed herein, rotation of the second wheel 50 in the direction Z causes the one or more stylets 2 to translate rearwardly within the housing 1 toward the loaded configuration.

Each of the first and second wheels 40, 50 pivotably receive a respective first and second connecting rod 30, 36 on a first end thereof 31, 37. The second end 32 of the first connecting rod 30 is pivotably connected to the cannula carrier 14, while the second end 38 of the second connecting rod 36 is pivotably connected to the stylet carrier 15. Each of the first and second connecting rods 30, 36 may be formed with a similar (or exactly the same) size and shape, or in other embodiments the design of the first and second connecting rods 30, 36 may differ as needed for size, space, or other considerations that would be apparent to one of skill in the art after understanding this specification and its various embodiments.

Figure 8:
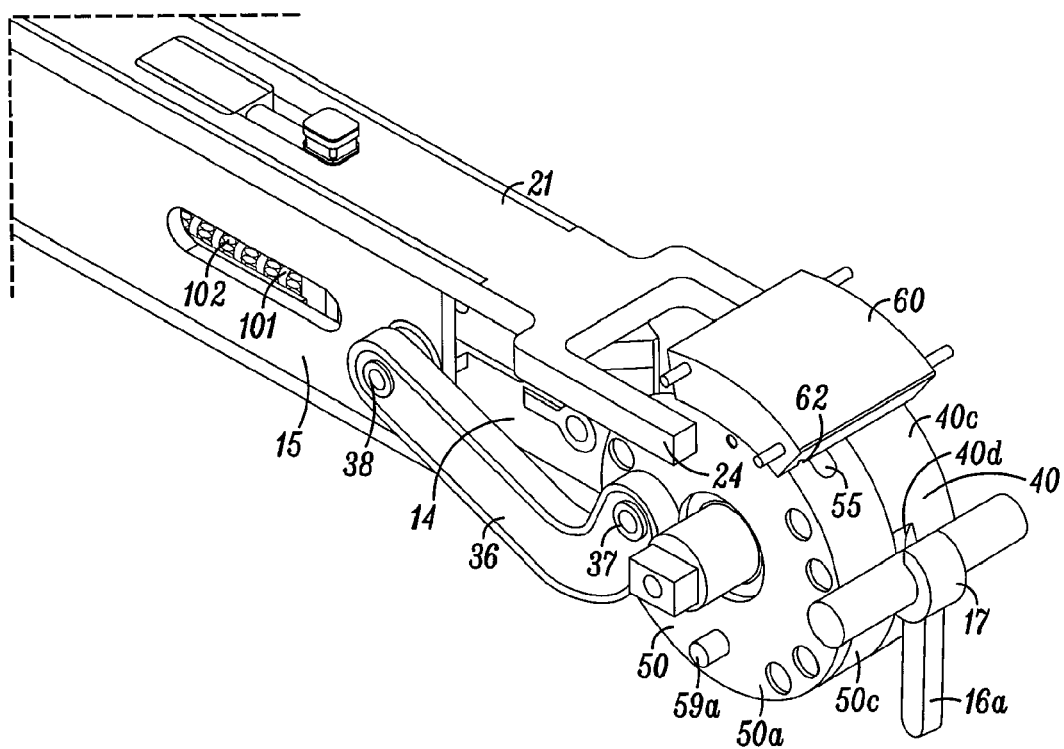
FIG. 8 is a perspective view of the instrument of FIG. 3, showing the second wheel and related components with the first wheel in loaded configuration.
Figure 9:
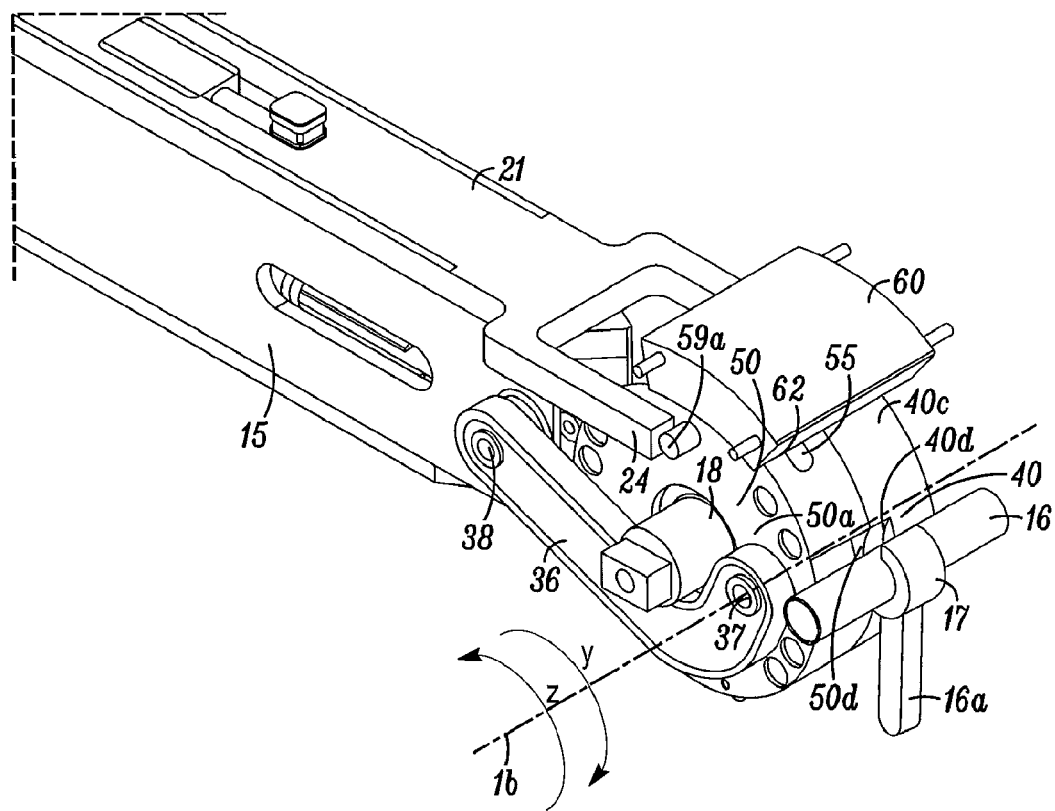
FIG. 9 is the view of FIG. 8 with the second wheel in the loaded configuration.

In some embodiments, best shown in FIGS. 2, 3, and 8, the first and second connecting rods 30, 36 may each be a substantially rigid member formed with an "L" shape. In some embodiments the respective first end 31, 37 of the first and second connecting rod 30, 36 may be disposed upon the shorter end of the "L" with the opposite second end 32, 38 of the respective connecting rod 30, 36 connected to the respective cannula or stylet carrier 14, 15. In some embodiments, the interior surface of each connection rod at the intersection between the legs of the "L" is arcuate and formed with a radius just larger than the radius of the outer surface of the axle 18. Accordingly, the inner surface of the respective connecting rod 30, 36 makes surface to surface contact (or is disposed very close to) the axle 18 when the respective connecting rod 30, 36 is in the loaded position (FIGS. 5, 9).

The first end 31, 37 of each connecting rod 30, 36 may be pivotably mounted to a pin that extends from the outer surface of the respective first or second wheel 40, 50, such that movement of the connecting rod urges rotation of the respective wheel and vice versa. In other embodiments, the connecting rods and wheels may be connected with other suitable structures. The pivotable connection between the first end 31, 37 of the respective connecting rod 30, 36 is such that rotation of the respective first or second wheel 40, 50 (as urged by the operator 6) in the direction Z causes the respective first or second connecting rod 30, 36 and specifically the first end 31, 37 of the connecting rod 30, 36, to translate in an arcuate path with rotation of the respective wheel 40, 50.

Figure 4:
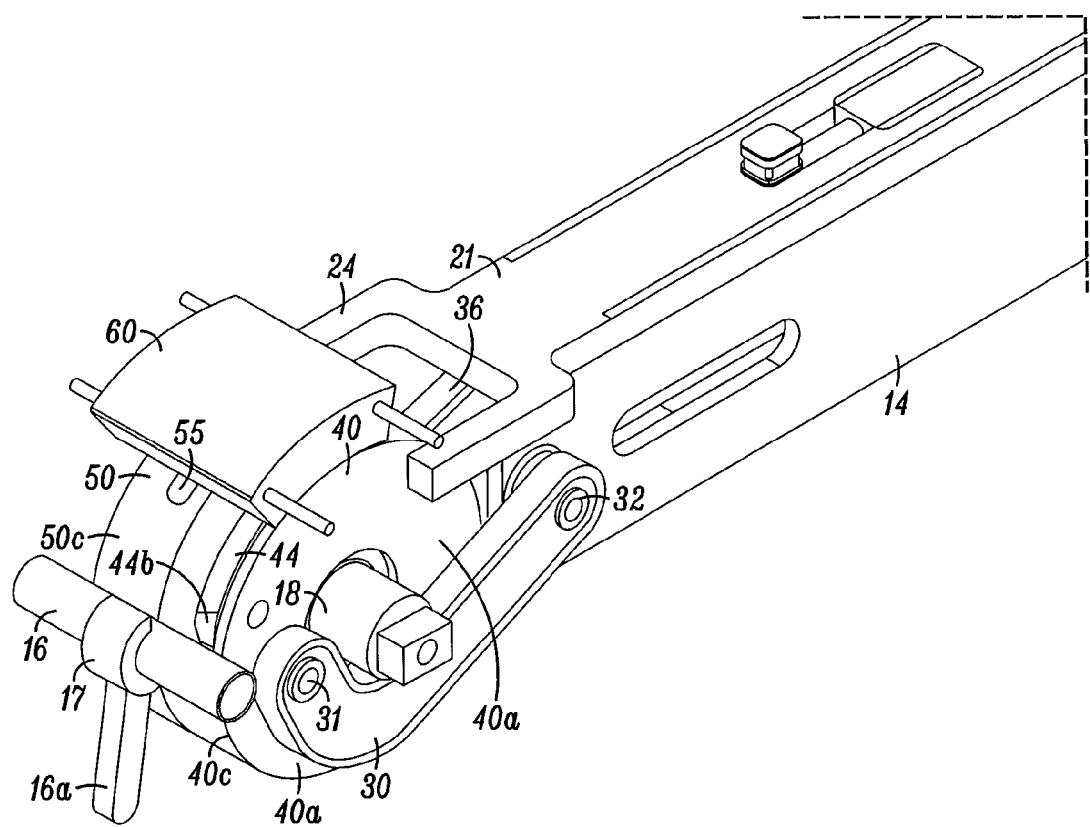
FIG. 4 is the view of FIG. 3 showing the first wheel partially rotated toward the loaded position.
Figure 5:
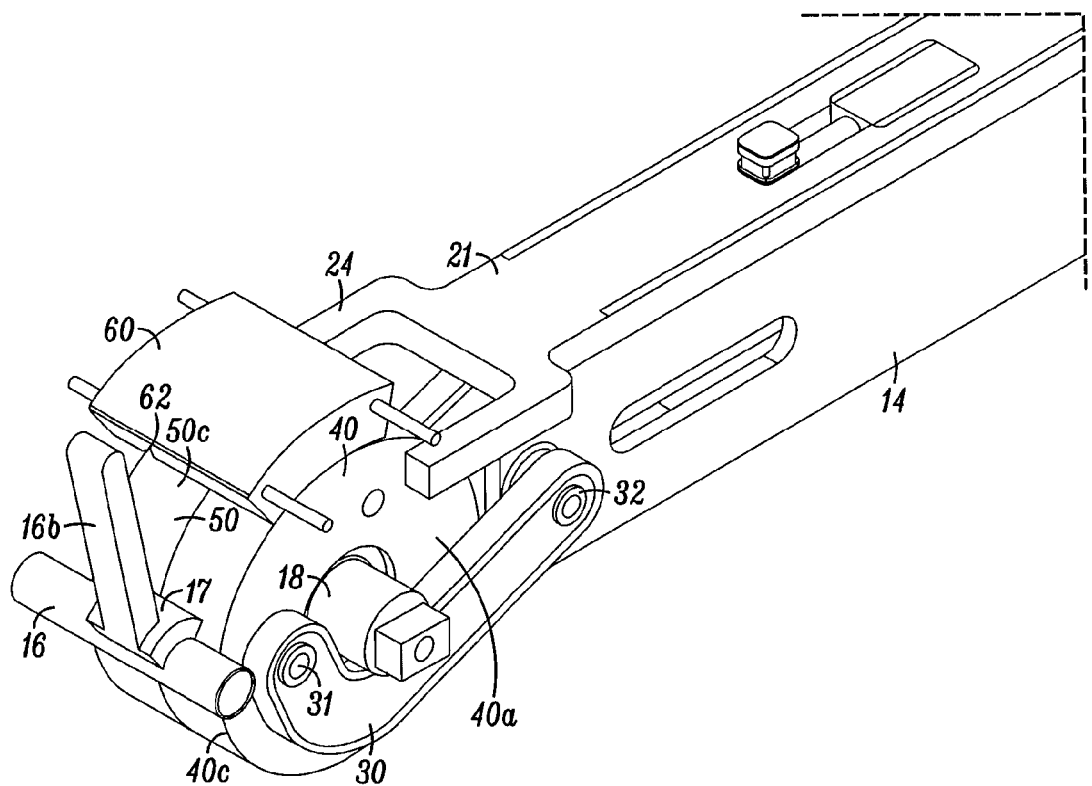
FIG. 5 is the view of FIG. 3 showing the first wheel in the loaded configuration with the safety engaging the first and second wheels.
Figure 5A:
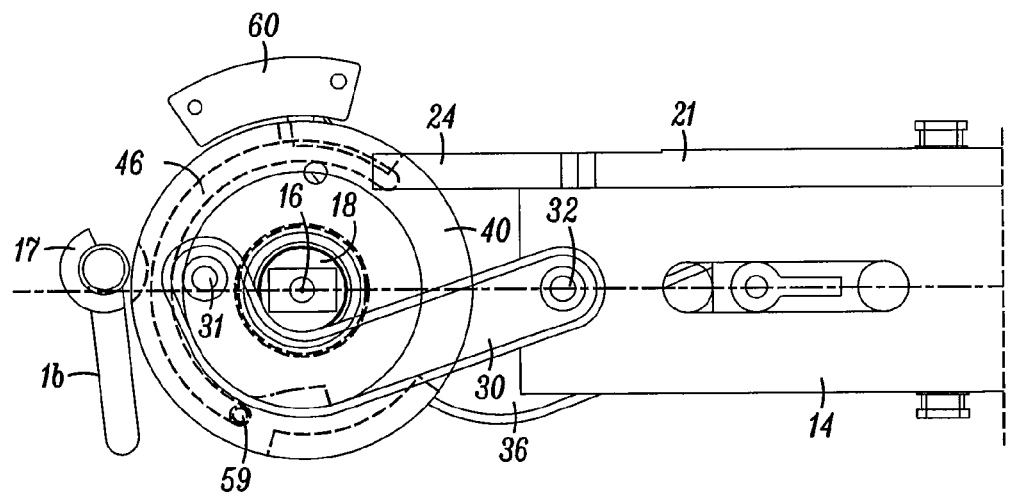
FIG. 5a is a side view of the configuration of FIG. 5.

Rotation of the first wheel 40 in the Z direction (due to rotation of the operator 6 and engagement between the tooth 18a of the axle 18 and the ledge 48 on the first wheel 40) causes the first connecting rod 30 to traverse the path depicted in the series of FIGS. 3-5, i.e. from a forward rest position (FIG. 3) to a rearward loaded position (FIG. 5). When the first connecting rod 30 is in the rearward position, a line of action 39a from the cannula spring 101 extends between the first and second ends 31, 32 and additionally extends through the center of the axle 18 (i.e. the axis 1b), or in the over center position. While the cannula spring 101 is constantly urging the cannula carrier 14 and the first connecting rod 30 connected thereto in the forward direction, the force applied to the first connecting rod 30 extends through the axle 18, which blocks forward motion of the first connecting rod 30 due to the engagement between first connection rod 30 and the axle 30. Further, because the line of action 39a extends through the axis of the first wheel 40, no torque is imparted upon the first wheel 40. The first connecting rod 30 and the first wheel 40 are maintained in the loaded position (i.e. the position causing the one or more cannulas 3 to be partially withdrawn within the housing 10) even after the operator 6 is let go and allowed to rotate in the direction Y to its rest position (FIG. 1) to a biasing member, such as a helical spring, urging the operator to the rest position.

The first end 37 of the second connecting rod 36 is pivotably connected to the second wheel 50 and the opposite second end 38 is pivotably connected to the stylet carrier 15 in a similar manner to the connection between the first wheel 40, the first connecting rod 30, and the cannula carrier 14. Specifically, as shown in FIGS. 8, 9, and 10a-11b, as the operator 6 is rotated a second time from the rest configuration in the direction Z, the axle 18 urges similar rotation of the second wheel 50 in the direction Z due to engagement between the pawl 56 and the tooth 18a of the axle 18. With continued rotation of the second wheel 50, the first end 37 of the second connecting rod 36 travels an arcuate path until the second connecting rod 36 is disposed such that a line of action 39b through the first and second ends 37, 38 of the second connecting rod 36 extends though the axle 18 and the rotational axis 1b. As with the first wheel 40 and first connecting rod 30, the second connecting rod 36 is prevented from forward translation due to engagement with the inner surface thereof and the axle 18 when in the loaded position, and the second wheel 50 and second connecting rod 36 do not feel any torque ultimately from the stylet spring X because the biasing force from the stylet spring X extends through the rotational axis 1b of the second wheel 50.

The first wheel 40 remains stationary in the loaded position when the operator 6 is rotated the second time in the direction Z (i.e. to load the one or more stylets 2 and the second wheel 50) because the tooth 18a does not contact the ledge 48 upon the first wheel 40. Similarly, the second wheel 50 does not rotate when the operator 6 is first rotated because the pawl 56 is positioned within the cutout 55 of the second wheel 50 and not in registry with the tooth 18a (due to engagement between the pawl 56 and the bottom surface of the shuttle 60). After the second wheel 50 is loaded the second wheel 50 remains in the loaded configuration after the operator 6 is released causing the operator 6 and axle 18 to rotate in the direction Y.

The instrument 10 further includes a firing mechanism 20 that is operable by the user to cause the one or more stylets 2 and then the one or more cannulas 3 to propel rapidly forward in succession to obtain a biopsy sample within the trough of the one or more stylets 2 of the patient's tissue. The firing mechanism 20 includes a button 22 that is disposed upon or in mechanical communication with an elongate fork 21. A proximal end 24 of the fork 21 is disposed proximate to the boss 59a that extends from the outer surface 50a of the second wheel 50 when the second wheel 50 is in the loaded position. The fork 21 may be biased forward within the housing 1 by a spring 103 (FIG. 2) or other biasing member to retain the fork 21 in a position where the proximal end 24 thereof is in close registration with but does not contact the boss 59a. In some embodiments, the button 22 may extend through an aperture in the housing 1 in a configuration to allow the user to manipulate the button 22 with the single hand that holds the instrument 10. Specifically, the housing 1 and button 22 may be configured such that the housing 1 is held with the user's fingers while the button 22 is operable with the user's thumb. The housing 1 may include a door or similar structure to selectively block access to the button 22 to prevent spurious operation of the firing mechanism 20.

With reference to FIG. 9, rearward translation of the button 22 causes the proximal end 24 of the fork 21 to slide in a similar manner until the proximal end 24 contacts the boss 59a. Because the boss 59a is aligned away from the axis 1b of the second wheel 50, translation of the boss 59a imparts a torque to the second wheel in the direction Y. As the second wheel 50 rotates, the line of action through the first and second ends 37, 38 of the second connecting rod 36 no longer passes directly through the central axis 1b of the second wheel 50, such that the forward biasing force imparted upon the second connecting rod 36 creates additional torque upon the second wheel 50 in the direction Y. Accordingly, the second wheel 50 accelerates and the stylet carrier 15 and one or more stylets 2 are accelerated in the forward direction, causing the stylets to impinge the patient's tissue.

As the second wheel 50 rotates in the Y direction the first wheel 40 remains stationary, such that the peg 59 extending from the inner surface 50b of the second wheel 50 travels along the length of the second slot 46 on the first wheel 40, from the second end 46b (where the peg 59 is normally disposed with respect to the second slot 46 when the first and second wheels 40, 50 are in the loaded configuration) toward the first end 46a of the second slot 46. In some embodiments, the peg 59 reaches the first end 46a of the second slot 46 when the one or more stylets 2 reach the relaxed position. In other embodiments, the relative sizes and configurations of the first and second wheels 40, 50 and the peg 59 and second slot 46 may be set such that the peg 59 reaches the first end 46a of the second slot 46 just before the one or more stylets 2 reach the relaxed position, or such that the peg 59 reaches the first end 46a of the second slot 46 during the travel of the one or more stylets 2, for example, when the stylets 2 have traveled about ¾, or about ⅝, or about ½ of their total length of travel.

The contact between the peg 59 and the first end 46a of the second slot 46 creates an impact force upon the first wheel 40 (due to the rotational momentum of the second wheel 50, which creates a torque in the direction Y upon the first wheel 40. The torque causes the first wheel 40 to rotate in the direction Y to a position where the line of action X through the first and second ends 31, 32 of the first connecting rod 30 no longer extend through the axis 1b of the first wheel 40, such that the forward biasing force imparted upon the first connecting rod 30 provides significantly more torque upon the first wheel 40, causing the cannula carrier 14 and one or more cannulas 3 to translate rapidly toward the first position.

As the first wheel 40 rotates in the direction Y, the rod 66 extending from the shuttle 60 into the first slot 44 in the first wheel 40 urges linear translation of the shuttle in the direction X (FIG. 10b) toward the first wheel 40 due to the curvature of the first slot 44. With motion of the shuttle 60 in the direction X, the upper engagement portion 56a of the pawl 56 no longer is in registry with the track 62 defined within the shuttle 60 and regains contact with the lower surface of the shuttle 60, causing the pawl 56 to rotate within the cutout 55 until the forward engagement portion 56b is no longer aligned for contact with the tooth 18a upon the axle 18.

After both the one or more stylets 2 and one or more cannulas 3 are moved forwardly into the rest position, the instrument 10 may be withdrawn from the patient and the one or more cannulas 3 may be again translated toward the loaded position to uncover the troughs in the one or more stylets 2 to removal of the biopsy sample collected therein. After the sample is removed, the instrument 10 may be returned to the rest position for further insertion and alignment with respect to the patient's tissue and may be again loaded as described herein.

As shown in FIGS. 1, 5, and 9, a safety 16 may be provided upon the instrument 10. The safety 16 may be a lever 16a that is rotatably mounted to the housing 10 with the lever 16a being manipulable by the user while holding the housing 10. The lever 16a may include a bulged portion 17 that radially extends from the lever only on a single side or through only a portion of the outer circumferential surface of the lever 16a. The bulged portion 17 and lever 16a are normally aligned such that the bulged portion 17 is not in engagement with the remaining portions of the operational mechanism of the instrument 10. As shown in FIGS. 5 and 9, each of the first and second wheels 40, 50 may include a cutout portion 40d, 50d that is in registry with the lever 16a, and specifically in registry to receive the bulged portion 17 within a void defined by the respective cutout portion 40d, 50d when each wheel 40, 50 is in the loaded position. Accordingly, when the first and second wheels 40, 50 are in the loaded position, the lever 16a may be rotated (FIG. 5) or translated until the bulged portion 17 is disposed within the void created by each cutout portion 40d, 50d, which prevents the first and second wheels 40, 50 from rotating, therefore preventing spurious and unintended firing of the instrument 10. The safety may be released to allow operation of the instrument 10 by moving the lever 16a such that the bulged portion 17 leaves the void of each cutout 40d, 50d therefore allowing the first and second wheels 40, 50 to rotate.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:

1. A biopsy instrument for obtaining a tissue biopsy sample, comprising:
   a housing that movably supports one or more elongate stylets and one or more elongate cannulas, each cannula comprising a lumen through which one of the one or more stylets is movably disposed therethrough;
   an operator rotatably mounted to the housing about an axis and fixed to an axle;
   a first wheel rotatable about the axis and in selective rotational connection with the axle, the first wheel operatively engaged with the one or more cannulas to cause translation of the one or more cannulas with rotation of the first wheel;
   a second wheel rotatable about the axis and in selective rotational connection with the axle, the second wheel operatively engaged with the one or more stylets to cause translation of the one or more stylets with rotation of the second wheel;
   a shuttle disposed within the housing and in selective connection with the first and second wheels, the shuttle being translatable about the housing, the shuttle comprising a pin that is received within a first slot defined about an outer circumference of the first wheel and selectively engageable with the second wheel to selectively allow torque transfer from the axle to the second wheel.

2. The biopsy instrument of claim 1, wherein the shuttle is translatable about the housing in a direction parallel to the axis.

3. The biopsy instrument of claim 1, further comprising a first connecting rod pivotably connected to the first wheel at a proximal end thereof and pivotably connected to a cannula carrier at a distal end thereof, the cannula carrier being fixedly connected to the one or more cannulas, and further comprising a second connecting rod pivotably connected to the second wheel at a proximal end thereof and pivotably connected to a stylet carrier at a distal end thereof, the stylet carrier fixedly connected to the one or more stylets.

4. The biopsy instrument of claim 3, wherein the first and second connecting rods are biased into a forward position and the first and second connecting rods are each separately translatable to a rear position where pivot connections in the proximal and distal ends of each of the respective first and second connecting rods are each aligned along a line that travels through the axis.

5. The biopsy instrument of claim 4, wherein the second wheel includes a pin that is received within an arcuate second slot disposed upon a side surface of the first wheel to allow limited rotation of the second wheel with respect to the first wheel and cause simultaneous rotation of the first and second wheels when the pin contacts an end of the second slot.

6. The biopsy instrument of claim 4, wherein the first slot is disposed upon the circumferential edge of the first wheel along an arc length that defines the arc length of rotation of the first wheel as the first connecting rod translates from the forward position to the rear position.

7. The biopsy instrument of claim 6, wherein at least a portion of the first slot is arcuately disposed upon the circumferential edge of the first wheel such that a first end of the first slot is proximate a first side surface of the first wheel and an opposite second end of the first slot is proximate an opposite second side surface of the first wheel, wherein engagement between the pin and the first slot causes the shuttle to translate as the first wheel rotates from a first position where the first connecting rod is in the forward position to a second position disposed away from the first side of the first wheel when the first connecting rod is in the rear position.

8. The biopsy instrument of claim 7, wherein the second wheel pivotably carries a movable pawl that contacts the shuttle, wherein the shuttle aligns the pawl in a first configuration to prevent rotational connection between the axle and second wheel when the shuttle is in the first position.

9. The biopsy instrument of claim 8, wherein translation of the shuttle to the second position aligns the pawl in a second configuration to allow rotational connection between the axle and second wheel.

10. The biopsy instrument of claim 4, wherein the biopsy instrument is configured such that a first rotation of the operator from a rest position urges the first connecting rod into the rear position and a subsequent second rotation of the operator from the rest position urges the second connecting rod into the rear position.

11. The biopsy instrument of claim 4, wherein each of the first and second wheels comprise a cutout upon a portion of an outer circumferential surface thereof, wherein the housing further comprises a lever movably disposed upon the housing, wherein the lever is configured to be selectively transferred and retained in a position with a portion thereof extending within the cutouts upon the first and second wheels when the first and second connecting rods are each in the second rear position.

12. The biopsy instrument of claim 4, further comprising a slider disposed within the housing and in registry with a boss extending from an outer surface of the second wheel when the second connecting rod is in the rear position, wherein the slider and boss are configured such that selective translation of the slider with respect to the housing impacts the boss and urges rotation of the second wheel allowing translation of the second connecting rod away from the rear position and toward the forward position.

13. A biopsy instrument comprising:
    a housing enclosing a translatable cannula carrier and a translatable stylet carrier, the stylet carrier disposed within at least a portion of the cannula carrier;
    one or more stylets fixed to the stylet carrier with a portion extending from the housing and one or more cannulas fixed to the cannula carrier, the one or more cannulas each extending from the housing with each of the one or more cannulas receiving a portion of one of the one or more stylets within a lumen of the cannula;
    a stylet and cannula operation mechanism comprising:
       a first wheel rotatably disposed within the housing upon an axle and a second wheel rotatably disposed within the housing upon the axle and rotatable with respect to the first wheel;
       a first connecting rod pivotably connected to each of the first wheel and the cannula carrier on opposite ends thereof and a second connecting rod pivotably connected to the second wheel and the stylet carrier on opposite ends thereof;
       an operator rotatably disposed upon the housing and configured such that a first rotation of the operator in a first direction from a rest position causes the first wheel to rotate in the first direction until a line through the opposite ends of the first connecting rod extends through the axle, and such that a second rotation of the operator in the first direction causes the second wheel to rotate in the first direction until a second line through the opposite ends of the second connecting rod extends through the axle.

14. The biopsy instrument of claim 13, wherein the second wheel comprises a pin that extends from an inner side surface of the second wheel and into an arcuate slot disposed upon an inner side surface of the first wheel, such that the second wheel is capable of rotation in a second direction opposite the first direction for an arc length within the arcuate slot and with additional rotation of the second wheel in the second direction the first wheel rotates along with the second wheel.

15. The biopsy instrument of claim 13, wherein the first wheel comprises a second slot disposed upon an outer circumferential surface thereof, wherein a first portion of the second slot is proximate an inner side surface of the first wheel and a second portion of the second slot is proximate an opposite outer side surface of the first wheel, wherein the second slot receives a pin that extends from a shuttle translatably disposed within the housing, such that the shuttle is in a first position when the pin is disposed in the first portion of the slot and is urged to a second position when the pin is disposed in the second portion of the slot.

16. The biopsy instrument of claim 15, wherein the second wheel comprises a movable pawl biased into a first outward position to prevent engagement between the operator and the second wheel through an axle fixed to the operator when the shuttle is in the first position, and the shuttle urges the pawl toward a second downwardly extending position as the shuttle translates toward the second position allowing engagement between the axle and the second wheel.

17. A mechanism for sequentially loading and unloading a biopsy instrument, comprising:
a first wheel operatively connected with a cannula, the first wheel rotatably mounted upon an axle such that the axle urges rotation of the first wheel in a first direction to transfer the cannula and the first wheel to a loaded position, the first wheel configured for selective rotation with respect to the axle in a second direction to transfer the cannula and the first wheel to an unloaded position;
a second wheel operatively connected with a stylet, the second wheel being configured to be rotated by the axle in the first direction when the first wheel is in the loaded position, the second wheel configured for rotation relative to the axle to transfer the stylet and second wheel from the loaded to unloaded position;
wherein the second wheel is operatively engaged with the first wheel to allow partial rotation of the second wheel in the second direction with respect to the first wheel and urging similar rotation of the first wheel in the second direction after at least some duration of relative rotation of the second wheel with respect to the first wheel.

18. The mechanism of claim 17, further comprising a shuttle that is slidably mounted with respect to an outer circumferential surface of each of the first and second wheels, the shuttle including a portion engaged with a portion of the first wheel to allow partial rotation of the first wheel but prevent full rotation of the first wheel.

19. The mechanism of claim 18, wherein the shuttle is slidable in a direction parallel to a rotational axis of the first and second wheels and is urged to slide with respect to the first and second wheels in response to rotation for the first wheel, wherein the shuttle is in a first position preventing engagement between the second wheel and the axle when the first wheel is in the unloaded position, and the shuttle is in a second position allowing engagement between the second wheel and the axle when the first wheel is in the loaded position.

20. The mechanism of claim 17, further comprising a firing mechanism disposed in concert with the first and second wheels, wherein the firing mechanism comprises a fork with a proximal end that is proximate to a peg upon the second wheel when the second wheel is in the loaded position, wherein the fork is configured to be urged toward the peg to impart a torque upon the second wheel in the second direction.

21. The mechanism of claim 17, further comprising a safety disposed in concert with the first and second wheels, wherein the safety comprises a movable lever with a bulged portion, wherein each of the first and second wheels comprise a cutout defined upon a portion of the outer circumferential surface thereof and when the first and second wheels are in the loaded position the respective cutouts in the first and second wheels are each configured to receive the bulged portion within a void defined by the cutouts.

* * * * *